(12) United States Patent
Vander Meer et al.

(10) Patent No.: US 10,093,928 B2
(45) Date of Patent: Oct. 9, 2018

(54) DOUBLE-STRANDED RNA CONSTRUCTS TO CONTROL INSECT PESTS

(75) Inventors: Robert K. Vander Meer, Newberry, FL (US); Man Yeon Choi, Gainesville, FL (US); Frederic Paul Schmitt, Saint Didier de Formans (FR); Cecile Denise Dorme, Lyons (FR); Angela Becker, Dusseldorf (DE)

(73) Assignees: The United States of America, as represented by The Secretary of Agriculture, Washington, DC (US); Bayer Cropscience AG, Monheim (DE)

( * ) Notice: Subject to any disclaimer, the term of this patent is extended or adjusted under 35 U.S.C. 154(b) by 1441 days.

(21) Appl. No.: 13/993,751

(22) PCT Filed: Dec. 14, 2011

(86) PCT No.: PCT/US2011/064816
§ 371 (c)(1),
(2), (4) Date: Jun. 13, 2013

(87) PCT Pub. No.: WO2012/082844
PCT Pub. Date: Jun. 21, 2012

(65) Prior Publication Data
US 2013/0305417 A1    Nov. 14, 2013

Related U.S. Application Data

(60) Provisional application No. 61/422,721, filed on Dec. 14, 2010.

(51) Int. Cl.
*C12N 15/82* (2006.01)
*C12N 15/113* (2010.01)
*A01N 57/16* (2006.01)
*A01N 63/02* (2006.01)

(52) U.S. Cl.
CPC .......... *C12N 15/1136* (2013.01); *A01N 57/16* (2013.01); *A01N 63/02* (2013.01); *C12N 15/8286* (2013.01)

(58) Field of Classification Search
CPC .................................................. C12N 15/1136
USPC ........................................................ 800/279
See application file for complete search history.

(56) References Cited

U.S. PATENT DOCUMENTS 9,617,542 B2 *   4/2017   Vander Meer ..... C12N 15/1136
2008/0124279 A1 *   5/2008   Andremont .......... A61K 9/5026
424/9.1

OTHER PUBLICATIONS

Thomas et al. 2001, The Plant Journal 25(4):417-425.*

* cited by examiner

*Primary Examiner* — Li Zheng
(74) *Attorney, Agent, or Firm* — John D. Fado; Mark D. McNemar

(57) ABSTRACT

Disclosed is a dsRNA construct that relates to a method to control insect pests of the genus *Helicoverpa* or *Heliothis* double-stranded RNA interference of the PBAN/Pyrokinin gene.

13 Claims, 6 Drawing Sheets

Specification includes a Sequence Listing.

DOUBLE-STRANDED RNA CONSTRUCTS TO CONTROL INSECT PESTS

CROSS-REFERENCE TO RELATED APPLICATION

This present application claims priority under 35 U.S.C. § 119(e) to U.S. Provisional Ser. No. 61/422,721, which was filed on Dec. 14, 2010 and PCT/US11/64816, which was filed on Dec. 14, 2011, titled "Double-Stranded RNA Constructs to Control Insect Pests", the complete subject matter of each of which are incorporated by reference herein by reference in their entirety.

FIELD OF THE INVENTION

This invention relates to a method to control a insect pests of the genus *Helicoverpa* or *Heliothis*, such as *Helicoverpa zea*, *Heliothis virescens*, and *Helicoverpa armigera*, via double-stranded RNA interference of the PBAN/Pyrokinin gene.

BACKGROUND OF INVENTION

Insect pests cost the general public billions of dollars annually in losses. These losses include the expense of controlling insect pests as well as crop loss and property damage caused by the pests. *Helicoverpa zea* has the capacity to inflict devastating yield losses to agronomically important crops. Depending the type of plant the larva of feeds on, the pest is also known as either cotton bollworm when it feeds on cotton, corn earworm when it feeds on corn. The treatment of *Helicoverpa zea* is typically controlled through the use of pyrethroid and *Bacillus thuringiensis* (Bt) insecticides.

*Heliothis virescens* (tobacco budworm) is found in the Americas, from Canada to Argentina. It is very similar to the closely-related genus *Helicoverpa*, under which name both genera were formerly subsumed. Due to its high reproductive potential, *H. virescens* may cause considerable losses, especially in cotton, tobacco and soybean, but also in alfalfa, cabbage, lettuce, okra, pea, pepper, squash, tomato and many others crops. *Helicoverpa armigera* (cotton bollworm) is almost indistinguishable from its near relative *H. zea*. However, the two species have different areas of distribution. *Helicaverpo armigera*, also called the "Old World bollworm", is found in parts of Europe, Asia, Africa and Australasia; *Helicoverpa zea*, the "New World Bollworm" in the Americas. Their host ranges are broadly similar.

Both species originate from tropical and subtropical regions, but they will immigrate over long distances into areas with temperate climates each summer. The adult insects are good fliers and are mostly active at night. *H. armigera* is very polyphageous, and is a pest of about 200 species. It also attacks a great number of cereal, vegetable and garden crops, among them beans, leek, zucchini, lemon, sunflower, artichoke, pigeonpea, sorghum and groundnut. Considered one of the most serious insect pests worldwide, causing huge losses due to its high reproductive potential and polyphagy. Economic damage is greatest in cotton and vegetables. In grain legumes, which are staple foods for people in many countries, up to 80% of the crop can be destroyed. *Helicovepa zea* (corn earworm) is pest to over 100 crop plants, the most important of which are corn, cotton and tomato. Other hosts include bean, broccoli, cabbage, eggplant, lettuce, okra, pea, pepper, soybean and watermelon. Corn earworm is found throughout the temperate and (sub)tropical parts of the Americas. It cannot overwinter successfully farther north than about 40° C. (104° F.); but being highly dispersive, it will immigrate into the northern USA and southern Canada each spring. Due to its high multiplication rate, *H. zea* can rapidly build up large populations, so the feeding caterpillars can sometimes cause devastating crop losses.

Chemical pesticides are the primary tools used to combat these insect pests. However, use of traditional chemical pesticides has disadvantages, including non-target effects on neutral or beneficial insects. Several microbial protein toxins such as the Cry or VIP proteins from Bacillus species (e.g., *Bacillus thuringiensis*) have been expressed in bacteria or plants to control plant pests (including *Helicoverpa* or *Heliothis* insect species). However, a constant exposure of the pest insects to these toxins is believed to eventually result in insect resistance development. Hence, new modes of action will be needed to control damaging plant pests such as *Helicoverpa* or *Heliothis* insects, particularly new modes of action unrelated to the toxins currently expressed in plants or chemistry applied on plants.

An approach to decrease dependence on chemical pesticides and provide for a new mode of action to reduce insect pest infestation is by causing a specific gene(s) of the target-pest to malfunction by either over expression or silencing gene expression. The silencing approach utilizes RNA interference pathways to knockdown the gene of interest via double-strand RNA. Double-strand RNA (dsRNA) induces sequence—specific post-transcriptional gene silencing in many organisms by a process known as RNA interference (RNAi). RNAi is a post-transcriptional, highly conserved process in eukaryotes that leads to specific gene silencing through degradation of the target mRNA. The silencing mechanism is mediated by dsRNA that is homologous in sequence to the gene of interest. The dsRNA is processed into small interfering RNA (siRNA) by an endogenous enzyme called DICER inside the target pest, and the siRNAs are then incorporated into a multi-component RNA-induced silencing complex (RISC), which finds and cleaves the target mRNA. The dsRNA inhibits expression of at least one gene within the target, which can exert a deleterious effect upon the target if that gene is required for normal development.

Fire, et al. (U.S. Pat. No. 6,506,559) disclose a process of introducing RNA into a living cell to inhibit gene expression of a target gene in that cell. The RNA has a region with double-stranded structure. Inhibition is sequence-specific in that the nucleotide sequences of the duplex region of the RNA and of a portion of the target gene are identical. Specifically, Fire, et al. (U.S. Pat. No. 6,506,559) disclose a method to inhibit expression of a target gene in a cell, the method comprising introduction of a double-stranded ribonucleic acid into the cell in an amount sufficient to inhibit expression of the target gene, wherein the RNA is a double-stranded molecule with a first ribonucleic acid strand consisting essentially of a ribonucleotide sequence which corresponds to a nucleotide sequence of the target gene and a second ribonucleic acid strand consisting essentially of a ribonucleotide sequence which is complementary to the nucleotide sequence of the target gene. Furthermore, the first and the second ribonucleotide strands are separate complementary strands that hybridize to each other to form the said double-stranded construct, and the double-stranded construct inhibits expression of the target gene. In using dsRNA in controlling a target insect, one method is to engineer a baculovirus to produce a dsRNA construct in vivo as disclosed in Liu, et al. (U.S. Pat. No. 6,846,482).

Salient to Liu is contacting an insect with a recombinant baculovirus wherein a first ribonucleic acid sequence corresponds to at least a portion of at least one gene endogenous to the insect to control the insect. Given the advances made in the field of transfection efficiency and RNA interference, there is a need in the art to utilize RNA interference technology without using a baculovirus as a vector. Such a method would mediate control of a target-pest without depending on variables associated with a baculovirus, such as expression and transfection of dsRNA by the baculovirus.

To utilize RNA interference as a method to regulate gene expression for control, a specific essential gene needs to be targeted. Genes associated with neurohormones represent novel potential targets. One neurohoromone gene family is the pheromone-biosynthesis-activating neuropeptide (PBAN)/pyrokinin gene family. The PBAN/pyrokinin gene produces multiple peptides, each of which are defined by a similar 5-amino-acid C-terminal sequence (FXPRLamide) that is the active core fragment for these peptides as reported in Raina, A. K. and T. G. Kempe (1992). "Structure activity studies of PBAN of *Helicoverpa zea* (Lepidoptera: Noctuidae)." Insect Biochem Mol Biol 22(3): 221-225. It was subsequently determined that the five C-terminal amino acids, FXPRLamide, represented the minimal sequence required for activity as reported in Raina, A. K. and T. G. Kempe (1992) id.; Fonagy, A., L. Schoofs, et al. (1992). "Functional cross-reactivities of some locustamyotropins and *Bombyx* pheromone biosynthesis activating neuropeptide." J Insect Physiol 38(9): 651-657; Kuniyoshi, H., H. Nagasawa, et al. (1992). "Cross-activity between pheromone biosynthesis activating neuropeptide (PBAN) and myotropic pyrokinin insect peptides." Biosci Biotechnol Biochem 56(1): 167-8; and Raina, A. K. and T. G. Kempe (1990). "A pentapeptide of the C-terminal sequence of PBAN with pheromonotropic activity." Insect Biochem 20(8): 849-851.

To date, over 200 PBAN/pyrokinin family peptides including peptides deduced from 40 species PBAN/pyrokinin genes have been identified. While it is one of the largest neuropeptide families in insects, the physiological functions of the PBAN/Pyrokinin peptides are only partially known. As such there is a need in the art to investigative whether the PBAN/Pyrokinin pathway can be used to interfere with essential developmental and/or reproductive functions of the targeted insect pests and result in abnormal development and/or lack of reproduction.

Furthermore there is a need for novel control methods that would interfere with essential developmental and/or reproductive functions of species that do not have the undesirable characteristics of traditional chemical pesticides. To that end, there is a need to develop dsRNA constructs that are engineered to interfere with essential developmental and/or reproductive functions of specific pest insects that would overcome some of the disadvantages of using traditional pesticides.

BRIEF SUMMARY OF THE INVENTION

Disclosed herein is a double-stranded ribonucleic acid (dsRNA) comprising a sense region with at least 94% sequence identity to SEQ. ID. NO. 4 and an antisense region comprising a second sequence complementary to said sense region. In one embodiment of the invention, the dsRNA sense region has at least 99% or has 100% sequence identity to SEQ. ID. NO. 4. In another embodiment of the invention, the antisense region comprises SEQ. ID. NO. 5. In yet another embodiment of the invention the double-stranded ribonucleic acid is expressed in a plant cell.

Also disclosed herein is a double-stranded ribonucleic acid (dsRNA) comprising a sense region comprising a sequence with at least 94% sequence identity to a portion of at least 19 consecutive nucleotides of a *Heliothis* PBAN/Pyrokinin gene, and an antisense region comprising a second sequence complementary to said sense region. In one embodiment of the invention, the sense region comprises a sequence with at least 94% sequence identity to a portion of at least 19 consecutive nucleotides in SEQ. ID. NO. 6 and an antisense region comprising a second sequence complementary to said sense region. In another embodiment of the invention, the antisense region comprises a portion of SEQ ID NO. 8. In yet another embodiment of the invention, the double-stranded ribonucleic acid is expressed in a plant cell.

Also disclosed herein is a double-stranded ribonucleic acid (dsRNA) comprising a sense region comprising a sequence with at least 94% sequence identity to a portion of at least 19 consecutive nucleotides of a *Heliothis* PBAN/Pyrokinin gene, and an antisense region comprising a second sequence complementary to said sense region where the sense region comprises a sequence with at least 94% sequence identity to a portion of at least 19 consecutive nucleotides in the RNA form of SEQ ID NO. 9, and an antisense region comprising a second sequence complementary to said sense region. In one embodiment of the invention, the antisense region comprises a portion of SEQ ID NO. 11. In yet another one embodiment of the invention, the double-stranded ribonucleic acid is expressed in a plant cell.

Also disclosed herein is a double-stranded ribonucleic acid (dsRNA) comprising a sense region comprising a sequence with at least 94% sequence identity to a portion of at least 19 consecutive nucleotides of a *Helicoverpa* PBAN/Pyrokinin gene, and an antisense region comprising a second sequence complementary to said sense region where the sense region comprises a sequence with at least 94% sequence identity to a portion of at least 19 consecutive nucleotides in the RNA form of SEQ. ID. NO. 1 and an antisense region comprising a second sequence complementary to said sense region.

Also disclosed herein is a DNA comprising a promoter functional in a host cell, and a DNA encoding a dsRNA comprising a first and a second region, wherein said first region comprises a sequence with at least 94% sequence identity to a portion of at least 19 consecutive nucleotides sequences of the sequence selected from the group consisting of: the RNA form of SEQ. ID. NO. 1, SEQ. ID. NO. 2, SEQ. ID. NO. 3, SEQ. ID. NO. 4, SEQ. ID. NO. 5, SEQ. ID. NO. 6, SEQ. ID. NO. 7, SEQ. ID. NO. 8, the RNA form of SEQ. ID. NO. 9, SEQ. ID. NO. 10, and SEQ. ID. NO. 11, and wherein said second region is complementary to said first region. In one embodiment of the invention, the host cell is a bacterial cell, a yeast cell, or a plant cell.

Also disclosed herein is a chimeric gene comprising the following operably linked DNA: (a) a plant-expressible promoter; (b) a DNA region which when transcribed yields a double-stranded RNA molecule targeting a PBAN/pyoki-nin gene of a *Helicoverpa* or *Heliothis* insect, said RNA molecule comprising a first and second RNA region wherein: (i) said first RNA region comprises a nucleotide sequence of at least 19 consecutive nucleotides having at least 94% sequence identity to the nucleotide sequence of said gene; (ii) said second RNA region comprises a nucleotide sequence complementary to said at least 19 consecutive nucleotides of said first RNA region; and (iii) said first and second RNA region are capable of base-pairing to form a double-stranded RNA molecule between at least said 19 consecutive nucleotides of said first and second region; and (c) optionally, a 3' end region comprising transcription termination and polyadenylation signals functioning in plant cells. In one embodiment of the invention, the first RNA region comprises a nucleotide sequence of at least 19 consecutive nucleotides having at least 95% sequence identity to a sequence selected from the group consisting of the sequence of SEQ. ID. NO. 2, 3, 4, 5, 6, 7, 8, 10, and 11, or of the sequence of the RNA form of SEQ ID NO. 1 or 9. In another embodiment of the invention, the said first RNA region comprises at least 19 consecutive nucleotides of the sequence of any one of SEQ ID NO. 2, 3, 4, 5, 6, 7, 8, 10, and 11, or of the sequence of the RNA form of SEQ ID NO. 1 or 9. In yet another embodiment of the invention, between said first and second RNA region, a spacer region containing a plant intron is present. In yet another embodiment of the invention, the first RNA region comprises a nucleotide sequence of at least 19 consecutive nucleotides which occurs with the same sequence or with at least 94% sequence identity in PBAN/pyrokinin genes of several Helicoverpa or Heliothis insects feeding on the same plant species. In one embodiment of the invention, the promoter is a constitutive promoter. In yet another embodiment of the invention, a plant cell, plant or seed comprising the chimeric gene or the double-stranded RNA molecule described above.

Also disclosed herein is a method to control a Heliothis or Helicoverpa insect, comprising applying to or in a material on which such insect feeds, a dsRNA targeted to a PBAN/pyrokinin gene of said insect. In one embodiment of the invention is a method of controlling a Helicoverpa or Heliothis insect, comprising planting or growing plants expressing a dsRNA that targets a PBAN/pyrokinin gene of said insect.

Also disclosed herein is a method for controlling a Helicoverpa or Heliothis species insect, the method comprising: applying a solution comprising copies of a double-stranded ribonucleic acid construct that targets a PBAN/Pyrokinin gene in said insect to plants or material on which said insect feeds. In one embodiment of the invention, the double-stranded ribonucleic acid targets the nucleotide sequence of at least one of SEQ. ID. NO. 2, 3, 4, 5, 6, 7, 8, 10 or 11, or the RNA form of SEQ ID NO 1 or 9.

BRIEF DESCRIPTION OF THE DRAWINGS

The present invention together with the disclosed embodiments may best be understood from the following detailed description of the drawings, wherein.

Figure 1:
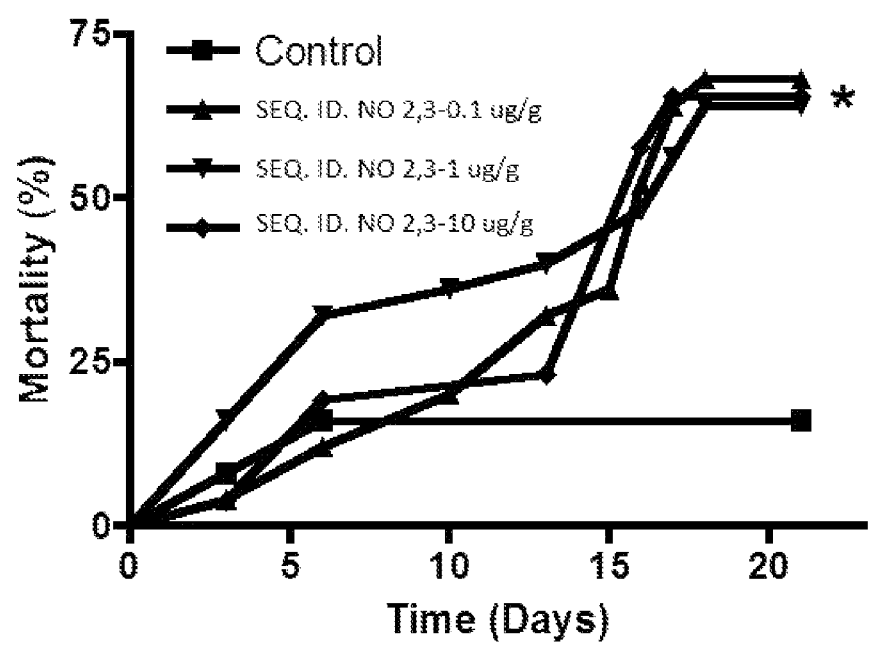
FIG. 1 is a graph depicting Helicoverpa zea larval mortality from first instar to just prior to pupation fed dsPBAN/pyrokinin treatment concentrations of 0.1 µg/1 g, 1 µg/1 g, or 10 µg/1 g of SEQ. ID. NO 2 and 3. The control diet was fed standard Helicoverpa zea diet (BioServe). Mortality curves were compared using the standard Kaplan-Meier Survival Analysis (GraphPad). Mortality for SEQ. ID. NO 2 and 3 treatment was significantly greater than the Control: Logrank test: $\chi^2=10.08$, df=1, P=0.0015. Since this concentration most closely followed the control, all dsPBANPyrokinin concentrations were significantly greater than the control. Comparison of the two most divergent dsPBAN/Pyrokinin concentrations showed no significant difference: Logrank test: $\chi^2=0.0537$, df=1, P=0.8167; therefore, results for the three treatment concentrations are not significantly different.
Figure 2:
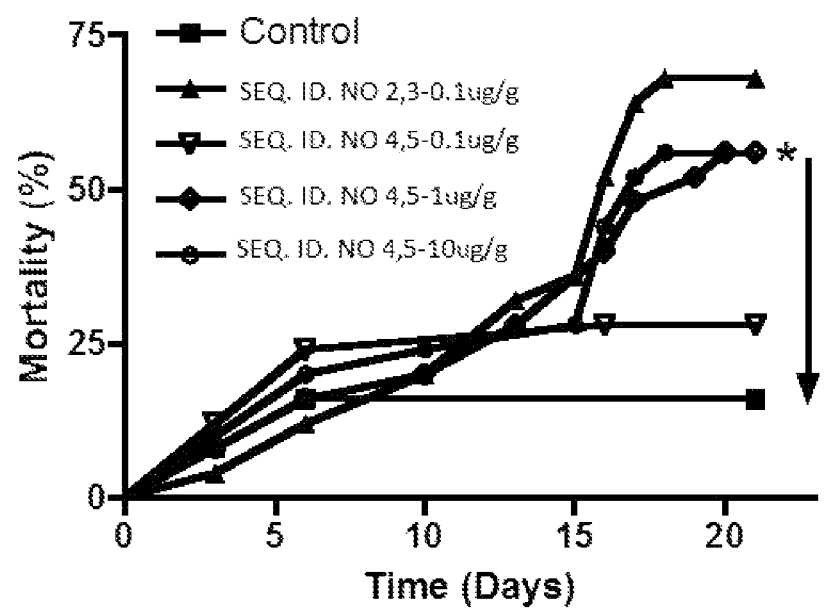
FIG. 2 is a graph depicting Helicoverpa zea larval mortality from first instar to just prior to pupation fed dsPBAN/pyrokinin treatment concentrations of 0.1 µg/1 g, 1 µg/1 g, or 10 µg/1 g of SEQ. ID. NO 4 and 5. A treatment of SEQ. ID. NO. 2 and 3 at 0.1 µg is also included. Results for SEQ. ID. NO 4 and 5 at 0.1 µg/1 g were not significantly different from the Control, nor different from the SEQ. ID. NO 4 and 5 at 10 µg/1 g: Logrank test: $\chi^2=0.9862$, df=1, P=0.3207; and $\chi^2=0.6441$, df=1, P=0.4222, respectively). In contrast mortality for SEQ. ID. NO 4 and 5 at 10 µg/1 g and therefore SEQ. ID. NO 4 and 5 at 1 µg/1 g was significantly greater than the Control: Logrank test: $\chi^2=7.019$, df=1, P=0.0081. In addition, results for SEQ. ID. NO 4 and 5 at 10 µg/1 g were not significantly different from SEQ. ID. NO 2 and 3 at 0.1 µg/1 g results: Logrank test, $\chi^2=0.6441$, df=1, P=0.4222 and by inference SEQ. ID. NO 4 and 5 at 1 µg/1 g results were not significantly different from SEQ. ID. NO 2 and 3 at 0.1 µg/1 g results.

The mean larval weight of PBAN SEQ. ID. NO. 2 and 3 at 10 ug/g concentration and SEQ. ID. NO. 4 and 5 at 1.0 ug/g were not significantly different (Two-tailed t-test: t=1.249, df=37, P=0.2196), therefore, the mean larval weights of the three SEQ. ID. NO. 4 and 5 concentrations were not different from SEQ. ID. NO. 2 and 3, and by inspection the results for the three SEQ. ID. NO. 4 and 5 concentrations were not different from the three PBAN SEQ. ID. NO. 2 and 3 concentrations. Thus, the 25 bp siRNA fragment mimicked the activity of the 508 bp dsPBAN/Pyrokinin construct.

BRIEF DESCRIPTION OF THE SEQUENCES

SEQ. ID. NO. 1:
ATGTTCAATCAAACTCAGTTGTTTGTTTTTCTCGCTGTATTCACTACGAG
CAGTGTTTTAGGGAATAACAATGATGTTAAGGATGGCGCAGCGAGTGGAG
CTCACAGCGACCGACTAGGTCTTTGGTTCGGTCCCCGGCTAGGCAAGCGC
TCGCTCAGAATATCTACCGAAGATAACAGACAAGCATTCTTCAAATTACT
CGAAGCCGCCGACGCTTTGAAATACTATTACGACCAGCTACCTTATGAGA
TGCAAGCTGATGAACCTGAAACCAGGGTCACCAAGAAGGTGATCTTCACC
CCCAAGTTAGGCAGAAGCCTCGCATACGATGACAAAAGCTTTGAGAACGT
GGAGTTCACGCCCAGACTCGGCAGGAGACTGTCCGATGATATGCCTGCCA
CCCCCGCTGACCAGGAAATGTACCGCCAAGACCCTGAACAGATTGACAGC
AGGACAAAGTACTTCTCCCCAAGGCTCGGCAGAACCATGAACTTCTCACC
ACGACTCGGCAGGGAACTGTCTTATGATATGATGCCAAATAAAATCAGGG
TAGTCAGGAGTACAAACAAAACGCGATCAACATAA is the PBAN/pyrokinin gene cDNA of *Helicoverpa zea*.

SEQ. ID. NO. 2 is a 5' to 3', 508 base pair construct forming one strand of the dsRNA product referred to as Hez-PBAN dsRNA construct.

SEQ. ID. NO. 2:
CAAUGAUGUUAAGGAUGGCGCAGCGAGUGGAGCUCACAGCGACCGACUAG
GUCUUUGGUUCGGUCCCCGGCUAGGCAAGCGCUCGCUCAGAAUAUCUACC
GAAGAUAACAGACAAGCAUUCUUCAAAUUACUCGAAGCCGCCGACGCUUU
GAAAUACUAUUACGACCAGCUACCUUAUGAGAUGCAAGCUGAUGAACCUG
AAACCAGGGUCACCAAGAAGGUGAUCUUCACCCCCAAGUUAGGCAGAAGC
CUCGCAUACGAUGACAAAAGCUUUGAGAACGUGGAGUUCACGCCCAGACU
CGGCAGGAGACUGUCCGAUGAUAUGCCUGCCACCCCCGCUGACCAGGAAA
UGUACCGCCAAGACCCUGAACAGAUUGACAGCAGGACAAAGUACUUCUCC
CCAAGGCUCGGCAGAACCAUGAACUUCUCACCACGACUCGGCAGGGAACU
GUCUUAUGAUAUGAUGCCAAAUAAAAUCAGGGUAGUCAGGAGUACAAACA
AAACGCGA.

SEQ. ID. NO. 3 is a 3' to 5', 508 base pair construct forming one strand of the dsRNA product referred to as Hez-PBAN dsRNA construct.

SEQ. ID. NO. 3:
GUUACUACAAUUCCUACCGCGUCGCUCACCUCGAGUGUCGCUGGCUGAUC
CAGAAACCAAGCCAGGGGCCGAUCCGUUCGCGAGCGAGUCUUAUAGAUGG
CUUCUAUUGUCUGUUCGUAAGAAGUUUAAUGAGCUUCGGCGGCUGCGAAA
CUUUAUGAUAAUGCUGGUCGAUGGAAUACUCUACGUUCGACUACUUGGAC
UUUGGUCCCAGUGGUUCUUCCACUAGAAGUGGGGGUUCAAUCCGUCUUCG
GAGCGUAUGCUACUGUUUUCGAAACUCUUGCACCUCAAGUGCGGGUCUGA
GCCGUCCUCUGACAGGCUACUAUACGGACGGUGGGGGCGACUGGUCCUUU
ACAUGGCGGUUCUGGGACUUGUCUAACUGUCGUCCUGUUUCAUGAAGAGG
GGUUCCGAGCCGUCUUGGUACUUGAAGAGUGGUGCUGAGCCGUCCCUUGA
CAGAAUACUAUACUACGGUUUAUUUUAGUCCCAUCAGUCCUCAUGUUUGU
UUUGCGCU.

SEQ. ID. NO. 4: is a 5' to 3', 25 base pair construct forming one strand of the dsRNA product referred to as siHez-PBAN dsRNA construct.

SEQ. ID NO. 4:
CGGCAGGGAACUGUCUUUAUGAUAUG.

SEQ. ID. NO. 5 is a 3' to 5', 25 base pair construct forming one strand of the dsRNA product referred to as siHez-PBAN dsRNA construct.

SEQ. ID. NO. 5:
GCCGUCCCUUGACAGAAUACUAUAC.

SEQ. ID. NO. 6:
AUGUUCUAUCAAACACAGUUAUUCGUUUUCCUCGCCGUCUUUGCGACUAC
CAGUGUUUUAGGAAAUAAUAAUGAUGAUAAGGAUGGCGCCGCCAGCGGGG
CGCACAGUGAUCGAUUAGGCCUUUGGUUCGGUCCCAGGUUAGGCAAACGA
UCUCUCAGGAUAUCUACGGGAGACAACAGGCAAGCAUUCUUCAAACUACU
GGAAGCAGCCGACGCUUUGAAAUACUACUACGACCAGCUGCCUUAUGAGA
UGCAAGCUGAUGACCCCGAAACCAGGGUGACCAAGAAGGUCAUCUUCACC
CCCAAGUUAGGCAGAAGCCUUUCAUAUGACGACAAGAGCUUUGAAAAUGU
GGAAUUCACGCCCAGGCUCGGAAGAAGAUUAGCUGAUGAUAUGCCCGCCA
CUCCUGCAGACCAGGAAAUGUACCGCCAAGACCCUGAACAGAUCGACAGC
AGGAGGACAAAGUACUUCUCCCCAAGACUUGGCAGGACUAUGAACUUCUC
CCCACGACUUGGCAGGGAACUGACUUAUGAUAUGCUGCCAAACAAAAUUA
GGGUCGUAAGGAGCACAAACAAAACGCGAUCAACGUAA is the mRNA PBAN/pyrokinin gene of *Heliothis virescens*.

SEQ. ID. NO. 7 is a 5' to 3', 476 base pair construct forming one strand of the dsRNA product referred to as Hev-PBAN dsRNA construct.

SEQ. ID. NO. 7:
CCGUCUUUGCGACUACCAGUGUUUUAGGAAAUAAUAAUGAUGAUAAGGAU
GGCGCCGCCAGCGGGGCGCACAGUGAUCGAUUAGGCCUUUGGUUCGGUCC
CAGGUUAGGCAAACGAUCUCUCAGGAUAUCUACGGGAGACAACAGGCAAG
CAUUCUUCAAACUACUGGAAGCAGCCGACGCUUUGAAAUACUACUACGAC
CAGCUGCCUUAUGAGAUGCAAGCUGAUGACCCCGAAACCAGGGUGACCAA
GAAGGUCAUCUUCACCCCCAAGUUAGGCAGAAGCCUUUCAUAUGACGACA
AGAGCUUUGAAAAUGUGGAAUUCACGCCCAGGCUCGGAAGAAGAUUAGCU
GAUGAUAUGCCCGCCACUCCUGCAGACCAGGAAAUGUACCGCCAAGACCC

-continued
UGAACAGAUCGACAGCAGGAGGACAAAGUACUUCUCCCCAAGACUUGGCA

GGACUAUGAACUUCUCCCCACGACUU.

SEQ. ID. NO. 8 is a 3' to 5', 476 base pair construct forming one strand of the dsRNA product referred to as Hev-PBAN dsRNA construct.

SEQ. ID. NO. 8:
GGCAGAAACGCUGAUGGUCACAAAAUCCUUUAUUAUUACUACUAUUCCUA

CCGCGGCGGUCGCCCCGCGUGUCACUAGCUAAUCCGGAAACCAAGCCAGG

GUCCAAUCCGUUUGCUAGAGAGUCCUAUAGAUGCCCUCUGUUGUCCGUUC

GUAAGAAGUUUGAUGACCUUCGUCGGCUGCGAAACUUUAUGAUGAUGCUG

GUCGACGGAAUACUCUACGUUCGACUACUGGGGCUUUGGUCCCACUGGUU

CUUCCAGUAGAAGUGGGGGUUCAAUCCGUCUUCGGAAAGUAUACUGCUGU

UCUCGAAACUUUUACACCUUAAGUGCGGGUCCGAGCCUUCUUCUAAUCGA

CUACUAUACGGGCGGUGAGGACGUCUGGUCCUUUACAUGGCGGUUCUGGG

ACUUGUCUAGCUGUCGUCCUCCUGUUUCAUGAAGAGGGGUUCUGAACCGU

CCUGAUACUUGAAGAGGGGUGCUGAA.

SEQ. ID. NO. 9:
ATCGTTCATTCCATGATGTTCAATCAAACTCAGTTGTTTGTTTTTCTCGC

TGTATTCACTACGAGCAGTGTTTTAGGGAATAACAATGATGTTAAGGATG

GCGCAGCGAGCGGGGCGCACAGCGACCGACTAGGCCTTTGGTTCGGTCCC

AGACTAGGCAAGCGCTCTCTCAGGATATCTACCGAAGATAACAGACAAGC

ATTCTTCAAATTACTGGAAGCTGCCGACGCTTTGAAATACTATTACGACC

AGCTACCTTATGAAATGCAAGCTGATGAACCTGAAACCAGGGTGACCAAG

AAGGTGATCTTCACCCCGAAGTTAGGCAGAAGCCTCGCATACGATGACAA

GAGCTTTGAAAACGTGGAGTTTACTCCTAGACTCGGCAGGAGACTGTCTG

ATGATATGCCTGCCACTCCCGCTGACCAGGAAATGTACCGCCAAGACCCT

GAACAAATTGACAGCAGGACGAAATACTTCTCCCCAAGGCTAGGCAGAAC

CATGAACTTCTCACCACGACTCGGCAGGGAACTGTCTTATGATATGATGC

CAAACAAAATCAGGGTAGTAAGGAGTGCAAACAAAACGCGATCAACATAA

TTTGGAGCAAAAACAAGACGCAAAGCTAGTCTAACCTCA is the 639 base pair PBAN/pyrokinin gene of Helicoverpa amigera.

SEQ. ID. NO. 10 is a 5' to 3', 500 base pair construct forming one strand of the dsRNA product referred to as HeA-PBAN dsRNA construct.

SEQ. ID. NO. 10:
UGGCAUCAUAUCAUAAGACAGUUCCCUGCCGAGUCGUGGUGAGAAGUUCA

UGGUUCUGCCUAGCCUUGGGGAGAAGUAUUUCGUCCUGCUGUCAAUUUGU

UCAGGGUCUUGGCGGUACAUUUCCUGGUCAGCGGGAGUGGCAGGCAUAUC

AUCAGACAGUCUCCUGCCGAGUCUAGGAGUAAACUCCACGUUUUCAAAGC

UCUUGUCAUCGUAUGCGAGGCUUCUGCCUAACUUCGGGGUGAAGAUCACC

UUCUUGGUCACCCUGGUUUCAGGUUCAUCAGCUUGCAUUUCAUAAGGUAG

-continued
CUGGUCGUAAUAGUAUUUCAAAGCGUCGGCAGCUUCCAGUAAUUUGAAGA

AUGCUUGUCUGUUAUCUUCGGUAGAUAUCCUGAGAGAGCGCUUGCCUAGU

CUGGGACCGAACCAAAGGCCUAGUCGGUCGCUGUGCGCCCCGCUCGCUGC

GCCAUCCUUAACAUCAUUGUUAUUCCCUAAAACACUGCUCGUAGUGAAU

A.

SEQ. ID. NO. 11 is a 3' to 5', 500 base pair construct forming one strand of the dsRNA product referred to as HeA-PBAN dsRNA construct.

SEQ. ID. NO. 11
ACCGUAGUAUAGUAUUCUGUCAAGGGACGGCUCAGCACCACUCUUCAAGU

ACCAAGACGGAUCGGAACCCCUCUUCAUAAAGCAGGACGACAGUUAAACA

AGUCCCAGAACCGCCAUGUAAAGGACCAGUCGCCCUCACCGUCCGUAUAG

UAGUCUGUCAGAGGACGGCUCAGAUCCUCAUUUGAGGUGCAAAAGUUUCG

AGAACAGUAGCAUACGCUCCGAAGACGGAUUGAAGCCCCACUUCUAGUGG

AAGAACCAGUGGGACCAAAGUCCAAGUAGUCGAACGUAAAGUAUUCCAUC

GACCAGCAUUAUCAUAAAGUUUCGCAGCCGUCGAAGGUCAUUAAACUUCU

UACGAACAGACAAUAGAAGCCAUCUAUAGGACUCUCUCGCAACGGAUCA

GACCCUGGCUUGGUUUCCGGAUCAGCCAGCGACACGCGGGGCGAGCGACG

CGGUAGGAAUUGUAGUAACAAUAAGGGAUUUUGUGACGAGCAUCACUUA

U.

DETAILED DESCRIPTION OF THE INVENTION

Disclosed here are specific insect pest dsRNA constructs that target PBAN/Pyrokinin genes in *Helicoverpa/Heliothis* insects. Using dsRNA inhibiting expression of the PBAN/Pyrokinin gene as a means of interfering with critical functions of the PBAN/Pyrokinin gene peptide products, a novel method for pest management is disclosed, as well as new products to control certain insect pests.

Definitions

As used in the specification and claims, the singular form "a", "an" and "the" include plural references unless the context clearly dictates otherwise. For example, the term "a cell" includes a plurality of cells, including mixtures thereof.

The term "gene" refers to a DNA sequence involved in producing a RNA or polypeptide or precursor thereof. The polypeptide or RNA can be encoded by a full-length coding sequence or by intron-interrupted portions of the coding sequence, such as exon sequences. In one embodiment of the invention, the gene target is a PBAN/Pyrokinin gene of a *Heliothis* or *Helicoverpa* insect, such as *Helicoverpa zea, Helicoverpa armigera, Helicoverpa assulta, Helicoverpa punctigera, Helicoverpa gelotopoeon*, or *Heliothis virescens, Heliothis punctifera*, or *Heliothis subflexa*.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. In one embodiment, the present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

As used herein, "dsRNA" refers to double-stranded RNA that comprises a sense and an antisense portion of a selected target gene (or sequences with high sequence identity thereto so that gene silencing can occur), as well as any smaller double-stranded RNAs formed therefrom by RNAse or dicer activity. Such dsRNA can include portions of single-stranded RNA, but contains at least 19 nucleotides double-stranded RNA. In one embodiment of the invention, the dsRNA is a hairpin RNA which contains a loop or spacer sequence between the sense and antisense sequences of the gene targeted, preferably such hairpin RNA spacer region contains an intron, particularly the rolA gene intron (Pandolfini et al., 2003, BioMedCentral (BMC) Biotechnology 3:7 (www.biomedcentral.com/1472-6750/3/7)), the dual orientation introns from pHellsgate 11 or 12 (see WO 02/059294 (incorporated by reference herein), and SEQ ID NO: 25 and 15 therein) or the pdk intron (*Flaveria trinervia* pyruvate orthophosphate dikinase intron 2; see WO99/53050 incorporated by reference).

Included in this definition are "siRNAs" or small interfering (double-stranded) RNA molecules of 16-30 bp, 19-28 bp, or 21-26 bp, e.g., such as the RNA forms that can be created by RNAseIII or dicer activity from longer dsRNA. siRNAs as used herein include any double-stranded RNA of 19 to 26, or 21 to 24 basepairs that can interfere with gene expression when present in a cell wherein such gene is expressed. siRNA can be synthetically made, expressed and secreted directly from a transformed cell or can be generated from a longer dsRNA by enzymatic activity. These siRNAs can be blunt-ended or can have overlapping ends. Also modified microRNAs comprising a portion of a selected PBAN/pyrokinin target gene and its complementary sequence are included herein as dsRNAs.

In one embodiment of this invention, dsRNA is used to control a *Helicoverpa* or *Heliothis* insect without such dsRNA being co-delivered with a transfection-promoting agent, although in some embodiments the dsRNA of the invention can be provided in a solution with a transfection-promoting agent. In one embodiment of the invention, the dsRNA is expressed in a plant to be protected, or in microorganisms which can be sprayed on plants to be protected. A "transfection promoting agent", as used herein, refers to a lipid-containing material that secures uptake into a cell of a dsRNA (hence crossing the cell membrane), particularly liposomes. Examples of such agents are described in published PCT patent application WO 03/004644.

The term "chimeric" when referring to a gene or DNA sequence is used to refer to a gene or DNA sequence comprising at least two functionally relevant DNA fragments (such as promoter, 5'UTR, coding region, 3'UTR, intron) that are not naturally associated with each other, such as a fusion of functionally relevant DNA fragments from different sources to form a plant-expressible chimeric gene expressing a dsRNA targeting a *Heliothis/Helicoverpa* PBAN/pyrokinin gene.

Sequences or parts of sequences which have "high sequence identity", as used herein, refers to the number of positions with identical nucleotides divided by the number of nucleotides in the shorter of the sequences, being higher than 95%, higher than 96%, higher than 97%, higher than 98%, higher than 99%, or between 96% and 100%. A target gene, or at least a part thereof, as used herein, preferably has high sequence identity to the dsRNA of the invention in order for efficient gene silencing to take place in the target pest. Identity in sequence of the dsRNA or siRNA with a part of the target gene RNA is included in the current invention but is not necessary.

For the purpose of this invention, the "sequence identity" of two related nucleotide or amino acid sequences, expressed as a percentage, refers to the number of positions in the two optimally aligned sequences which have identical residues ($\times 100$) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch 1970). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

For the purpose of the invention, the "complement of a nucleotide sequence X" is the nucleotide sequence which would be capable of forming a double-stranded DNA molecule with the represented nucleotide sequence, and which can be derived from the represented nucleotide sequence by replacing the nucleotides by their complementary nucleotide according to Chargaff's rules (A< >T; G< >C) and reading in the 5' to 3' direction, i.e., in opposite direction of the represented nucleotide sequence.

In one embodiment of the invention, sense and antisense RNAs can be separately expressed in vitro or in host cells, e.g., from different chimeric gene constructs using the same or a different promoter or from a construct containing two convergent promoters in opposite orientation. These sense and antisense RNAs which are formed, e.g., in the same host cells, can then combine to form dsRNA. It is clear that whenever reference is made herein to a dsRNA chimeric gene or a dsRNA molecule, that such dsRNA formed, e.g., in plant cells, from sense and antisense RNA produced separately is also included. Also synthetically made dsRNA annealing RNA strands are included herein when the sense and antisense strands are present together.

A dsRNA "targeting" a *Helicoverpa* or *Heliothis* PBAN/pyrokinin insect gene, as used herein, refers to a dsRNA that is designed to be identical to or have high sequence identity to an endogenous PBAN/pyrokinin insect gene of *Heliothis* or *Helicoverpa* insects (the target gene), and as such is designed to silence such gene upon application to such insect or to plants fed on by such insects. One dsRNA can target one or several homologous PBAN/Pyrokinin target genes in one insect or one or several homologous target genes in different insects which can feed on the same host plant. In one embodiment, the dsRNA of the invention targets a PBAN/pyrokinin gene in both a *Helicoverpa* and a *Heliothis* pest insect, such as a dsRNA targeting a PBAN/pyrokinin gene in *Helicoverpa zea* and in *Heliothis virescens*, or a dsRNA targeting a PBAN/pyrokinin gene in *Helicoverpa zea, Helicoverpa amirgera* and *Heliothis virescens*.

The dsRNA chimeric gene, encoding a dsRNA targeting a PBAN/pyrokinin gene, can be stably inserted in a conventional manner into the genome of a single plant cell, and the so-transformed plant cell can be used in a conventional manner to produce a transformed plant that has increased insect resistance. In this regard, a disarmed Ti-plasmid, containing the dsRNA chimeric gene, in *Agrobacterium tumefaciens* can be used to transform the plant cell, and thereafter, a transformed plant can be regenerated from the transformed plant cell using the procedures described in the art, for example, in EP 0 116 718, EP 0 270 822, PCT publication WO 84/02913 and published European Patent application ("EP") 0 242 246. Preferred Ti-plasmid vectors each contain the dsRNA chimeric gene between the border sequences, or at least located to the left of the right border sequence, of the T-DNA of the Ti-plasmid. Of course, other types of vectors can be used to transform the plant cell, using procedures such as direct gene transfer (as described, for example in EP 0 233 247), pollen mediated transformation (as described, for example in EP 0 270 356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., 1990, Bio/Technology 8, 833-839); Gordon-Kamm et al., 1990, The Plant Cell 2, 603-618) and rice (Shimamoto et al., 1989, Nature 338, 274-276; Datta et al., 1990, Bio/Technology 8, 736-740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (1988, Bio/Technology 6, 915) and Christou et al. (1990, Trends Biotechnology 8, 145) or the method of WO 00/42207.

The resulting transformed plant can be used in a conventional plant breeding scheme to produce more transformed plants with the same characteristics or to introduce the dsRNA chimeric gene in other varieties of the same or related plant species. Seeds, which are obtained from the transformed plants, contain the dsRNA gene as a stable genomic insert. Plants comprising a dsRNA in accordance with the invention include plants comprising or derived from root stocks of plants comprising the dsRNA chimeric gene of the invention, e.g., fruit trees or ornamental plants. Hence, any non-transgenic grafted plant parts inserted on a transformed plant or plant part are included in the invention since the RNA interference signal is transported to these grafted parts and any insects feeding on such grafted plant are similarly affected by the dsRNA or siRNA of the invention.

A DNA encoding a dsRNA is inserted in a plant cell genome so that this DNA is downstream (i.e., 3') of, and operably linked to, a plant-expressible promoter which can direct expression in plant cells. This is preferably accomplished by inserting the dsRNA chimeric gene in the plant cell genome, particularly in the nuclear or plastid (e.g., chloroplast) genome.

A 'plant-expressible promoter' as used herein refers to a promoter that ensures expression of a dsRNA of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., 1981, Nucleic Acids Research 9, 2871-2887), CabbB-S (Franck et al., 1980, Cell 21, 285-294) and CabbB-JI (Hull and Howell, 1987, Virology 86, 482-493); promoters from the ubiquitin family (e.g., the maize ubiquitin promoter of Christensen et al., 1992, Plant Mol. Biol. 18, 675-689), the gos2 promoter (de Pater et al., 1992, The Plant J. 2, 834-844), the emu promoter (Last et al., 1990, Theor. Appl. Genet. 81, 581-588), actin promoters such as the promoter described by An et al. (1996, The Plant J. 10, 107), the rice actin promoter described by Zhang et al. (1991, The Plant Cell 3, 1155-1165); promoters of the Cassava vein mosaic virus (WO 97/48819, Verdaguer et al. (1998, Plant Mol. Biol. 37, 1055-1067), the pPLEX series of promoters from Subterranean Clover Stunt Virus (WO 96/06932, particularly the S4 or S7 promoter), a alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984, EMBO J 3, 2723-2730). Alternatively, a plant-expressible promoter can be a tissue-specific promoter, i.e., a promoter directing a higher level of expression in some cells or tissues of the plant, e.g., in green tissues (such as the promoter of the PEP carboxylase). The plant PEP carboxylase promoter (Pathirana et al., 1997, Plant J. 12:293-304) has been described to be a strong promoter for expression in vascular tissue and is useful in one embodiment of the current invention. Alternatively, a plant-expressible promoter can also be a wound-inducible promoter, such as the promoter of the pea cell wall invertase gene (Zhang et al., 1996, Plant Physiol. 112:1111-1117). A 'wound-inducible' promoter as used herein means that upon wounding of the plant, either mechanically or by insect feeding, expression of the coding sequence under control of the promoter is significantly increased in such plant.

These plant-expressible promoters can be combined with enhancer elements, they can be combined with minimal promoter elements, or can comprise repeated elements to ensure the expression profile desired.

Elements which can be used to increase expression in plant cells can be: an intron at the 5' end or 3' end of the chimeric gene, or in the coding sequence of the chimeric dsRNA gene (such as between the region encoding the sense and antisense portion of the dsRNA), e.g., the hsp70 intron, besides promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

The dsRNA chimeric gene of the invention can be inserted in the plant genome so that the inserted gene part is upstream (i.e., 5') of suitable 3' end transcription regulation signals (i.e., transcript formation and polyadenylation signals). This is preferably accomplished by inserting the dsRNA chimeric gene in the plant cell genome. Preferred polyadenylation and transcript formation signals include those of the nopaline synthase gene (Depicker et al., 1982, J. Molec. Appl. Genetics 1, 561-573), the octopine synthase gene (Gielen et al., 1984, EMBO J. 3:835-845), the SCSV or the Malic enzyme terminators (Schunmann et al., 2003, Plant Functional Biology 30:453-460), and the T-DNA gene 7 (Velten and Schell, 1985, Nucleic Acids Research 13, 6981-6998), which act as 3'-untranslated DNA sequences in transformed plant cells.

The dsRNA chimeric gene can optionally be inserted in the plant genome as a hybrid gene, containing several dsRNA regions which target different PBAN/pyrokinin genes in different *Heliothis* or *Helicoverpa* insects, or which target different portions of the same PBAN/pyrokinin target gene, or target different PBAN/pyrokinin alleles in the same insect. Also, it is convenient to include in the transforming DNA of the invention also a selectable or scorable marker gene, such as the bar, epsps or the neo gene, so that transformed plants can easily be selected by application of glufosinate, glyphosate or kanamycin, respectively, as is well known in the art. Advantageously, the plants or seeds of the invention also comprise a glufosinate or glyphosate tolerance gene besides the dsRNA chimeric gene of the invention, so that plants can be selected using application of the relevant herbicide (glufosinate or glyphosate).

Although plant delivery of a dsRNA is an embodiment of this invention, in accordance with this invention, application of the dsRNA of the invention can be done in several ways, and need not be by way of a plant expressing a dsRNA. Any method of delivery of dsRNA not contained in a plant cell is included herein, e.g., in vitro or in vivo produced dsRNA applied to an insect diet or feed, or microbially- or yeast-expressed dsRNA. dsRNA can be applied on plants on which *Helicoverpa* or *Heliothis* insects feed by spraying a solution or microbial/yeast spores/cells comprising the dsRNA of the invention.

"Insecticidal activity" of a dsRNA, as used herein, refers to the capacity to obtain mortality in insects when such dsRNA is fed to insects, preferably by expression in a recombinant host such as a plant, which mortality is significantly higher than a negative control (using a non-insect dsRNA or buffer). "Insect-control" of a dsRNA, as used herein, refers to the capacity to inhibit the insect development, fertility, inhibition of pheromone production, or growth in such a manner that the insect population provides less damage to a plant, produces fewer offspring, are less fit or are more susceptible to predator attack, or that insects are even deterred from feeding on such plant.

Information on how to design optimal dsRNA sequences once a target gene is known can be found with commercial providers, e.g., the companies Ambion and Cenix BioScience (Ambion Inc., 2130 Woodward Street, Austin, Tex. 78744-1832, USA; and see www.ambion.com; and Cenix BioScience GmbH, Pfotenhauerstr. 108, 01307 Dresden, Germany, see www.cenix-bioscience.com). Preferably, the dsRNAs to be used in this invention target at least one PBAN/pyrokinin *Heliothis* or *Helicoverpa* insect gene, or a PBAN/pyrokinin insect gene portion of at least 19 consecutive nucleotides occurring in identical sequence or with high sequence identity in a several *Heliothis* or *Helicoverpa* insect pests feeding on the same plant species, such as in *Heliothis virescens, Helicoverpa armigera* and *Helicoverpa zea*. In one embodiment of this invention, such dsRNAs do not silence genes of the plant host or of other non-target animals, such as *Heliothis/Helicoverpa* insect predators or animals such as reptiles, amphibians, birds, or mammals. This can be analyzed in available databases, e.g., by a BLAST search (see also www.ncbi.nlm.nih.gov/BLAST) or by hybridization with existing DNA libraries of representative non-target organisms. In one embodiment, a portion of a target PBAN/pyrokinin gene sequence is selected which is present in several *Helicoverpa* and/or *Heliothis* insects of a plant host in identical sequence or with high sequence identity, of a length sufficient to be capable of silencing the PBAN/pyrokinin gene.

In one embodiment of this invention, the dsRNA or siRNA of the invention corresponds to an exon in the target gene.

Also, in the dsRNA chimeric gene of the invention a nuclear localization signal can be added as described in published US patent application 20030180945 (incorporated herein by reference).

As used herein, nucleotide sequences of RNA molecules may be identified by reference to DNA nucleotide sequences of the sequence listing. However, the person skilled in the art will understand whether RNA or DNA is meant depending on the context. Furthermore, the nucleotide sequence is identical except that the T-base is replaced by uracil (U) in RNA molecules.

The length of the first (e.g., sense) and second (e.g., antisense) nucleotide sequences of the dsRNA molecules of the invention may vary from about 10 nucleotides (nt) up to a length equaling the length in nucleotides of the transcript of the target gene. The length of the first or second nucleotide sequence of the dsRNA of the invention can be at least 15 nt, or at least about 20 nt, or at least about 50 nt, or at least about 100 nt, or at least about 150 nt, or at least about 200 nt, or at least about 400 nt, or at least about 500 nt. If not all nucleotides in a target gene sequence are known, it is preferred to use such portion for which the sequence is known and which meets other beneficial requirements of the invention.

It will be appreciated that the longer the total length of the first (sense) nucleotide sequence in the dsRNA of the invention is, the less stringent the requirements for sequence identity between the total sense nucleotide sequence and the corresponding sequence in the target gene becomes. The total first nucleotide sequence can have a sequence identity of at least about 75% with the corresponding target sequence, but higher sequence identity can also be used such as at least about 80%, at least about 85%, at least about 90%, at least about 95%, about 100%. The first nucleotide sequence can also be identical to the corresponding part of the target gene. However, it is advised that the first nucleotide sequence includes a sequence of 19 or 20, or about 19 or about 20 consecutive nucleotides, or even of about 50 consecutive nucleotides, or about consecutive 100 nucleotides, or about 150 consecutive nucleotides with only one mismatch, preferably with 100% sequence identity, to the corresponding part of the target gene. For calculating the sequence identity and designing the corresponding first nucleotide sequence, the number of gaps should be minimized, particularly for the shorter sense sequences.

The length of the second (antisense) nucleotide sequence in the dsRNA of the invention is largely determined by the length of the first (sense) nucleotide sequence, and may correspond to the length of the latter sequence. However, it is possible to use an antisense sequence which differs in length by about 10% without any difficulties. Similarly, the nucleotide sequence of the antisense region is largely determined by the nucleotide sequence of the sense region, and may be identical to the complement of the nucleotide sequence of the sense region. Particularly with longer antisense regions, it is however possible to use antisense sequences with lower sequence identity to the complement of the sense nucleotide sequence, such as at least about 75% sequence identity, or least about 80%, or at least about 85%, more particularly with at least about 90% sequence identity, or at least about 95% sequence to the complement of the sense nucleotide sequence. Nevertheless, it is advised that the antisense nucleotide sequence always includes a sequence of 19 or 20, about 19 or about 20 consecutive nucleotides, although longer stretches of consecutive nucleotides such as about 50 nucleotide, or about 100 nucleotides, or about 150 nucleotides with no more than one mismatch, preferably with 100% sequence identity, to the complement of a corresponding part of the sense nucleotide sequence can also be used. Again, the number of gaps should be minimized, particularly for the shorter (19 to 50 nucleotides) antisense sequences.

In one embodiment of the invention, the DNA molecules according to the invention may comprise a DNA region encoding a spacer between the DNA region encoding the first and second nucleotide sequences. As indicated in WO 99/53050 the spacer may contain an intron to enhance gene silencing. A particularly preferred intron functional in cells of plants is the pdk intron (*Flaveria trinervia* pyruvate orthophosphate dikinase intron 2; see WO99/53050 incorporated by reference), the delta 12 desaturase intron from *Arabidopsis* (Smith et al., 2000, Nature 407:319-20) or the intron of the rolA gene (Magrelli et al., 1994, Science 266:1986-1988; Spena and Langenkemper, 1997, Genet. Res. 69:11-15).

In one embodiment of the invention, the dsRNA molecule may further comprise one or more regions having at least 94%, at least 95%, at least 96%, at least 97%, at least 98%, or at least 99%, sequence identity to regions of at least 19 consecutive nucleotides from the sense nucleotide sequence of the target gene, different from the at least 19 consecutive nucleotides as defined in the first region, and one or more regions having at least 94%, at least 95%, at least 96%, at least 97%, at least 98%, or at least 99%, sequence identity to at least 19 consecutive nucleotides from the complement of the sense nucleotide sequence of the target gene, different from the at least 19 consecutive nucleotides as defined in the second region, wherein these additional regions can basepair amongst themselves.

"Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene As used herein, the term "GFP dsRNA" refers to a control dsRNA construct targeting a GFP sequence. The green fluorescent protein (GFP) is commonly used as a reporter gene and was originally isolated from jellyfish and widely used as control in prokaryotic and eukaryotic systems.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA". An "RNA form" of a DNA sequence, as used herein is the RNA sequence of said DNA, so the same sequence but wherein the T nucleotide is replaced by an U nucleotide.

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target insect wherein critical developmental and/or reproductive functions of said insect are disrupted as a result of ingestion.

The term "solvent" includes any liquid that holds another substance in solution. Examples of solvents include but are not limited to water and organic solvents such as acetone, ethanol, dimethyl sulfoxide (DMSO), and dimethylformamide (DMF).

The term "phagostimulant" refers to any substance that will entice the insect to ingest the dsRNA. For insects, suitable phagostimulants include but are not limited to syrups, honey, aqueous solutions of sucrose, artificial sweeteners such as sucralose, saccharin, and other artificial sweeteners, and amino acids.

Methods which are well known to those skilled in the art may be used to construct expression vectors containing sequences encoding PBAN/Pyrokinin gene and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) Current Protocols in Molecular Biology, John Wiley & Sons, New York, N.Y.

For the oral delivery of a dsRNA construct to insects, the dsRNA construct or siRNA was dissolved in nuclease-free water or water (negative control) was mixed with a specific artificial diet for *Helicoverpa zea* (BioServ) or *Heliothis virescens* (BioServ) or *Helicoverpa armigera*. Below in Table 1 details the noctuid diet.

TABLE 1

| | |
|---|---:|
| Water | 183.00 l |
| Agar agar (700-800 Gel) | 4.40 kg |
| Plant oil | 120.00 ml |
| Wesson's Salt Mix | 140.00 g |
| Sorbic acid | 720.00 g |
| 4-Hydroxybenzoeacidmethylester (99%) | 600.00 ml |

TABLE 1-continued

| | |
|---|---|
| Formaldehyde | 480.00 ml |
| Sitosterin | 120.00 g |
| L-Leucin | 100.00 g |
| L-(+)-Ascorbic acid | 800.00 g |
| Bioserve Vitamine Mixture | 740.00 g |
| Beer yeast extract powder | 8.00 kg |
| Alfalfa Leaf powder | 3.60 kg |
| Bean powder | 26.60 kg |
| Chlortetracyclin | 100.00 g |

The treatments or controls and diet were mixed when the freshly made diet had cooled to 65° C., before the diet solidified. Three concentrations were prepared: 0.1 µg/g diet, 1.0 µg/g diet, and 10 µg/g diet. The diet was provided from 1$^{st}$ instar of the insect until pupation in an individual container. GFP dsRNA and water without dsRNA were used for negative controls. In the case of *Helicoverpa zea, Heliothis virescens*, and *Helicoverpa armigera* larvae were reared at 25±1° C. and 60±5% relative humidity under L16:D8 photoperiod.

While the examples provided wherein describe dsRNA constructs cloned from GenBank Accession Nos. U08109 (*Helicoverpa zea*), AY173075 (*Heliothis virescens*), and AY43222 (*Helicoverpa amigera*) it is contemplated that when read in conjunction with the teaching disclosed herein and the knowledge in the art, the construction of other dsRNA constructs targeting PBAN/pyrokinin gene sequences of other *Helicoverpa* or *Heliothis* insect species would be feasible to those skilled the in the art. For example, including but not limited to the PBAN/pyrokinin gene/amino acid sequences disclosed in Table 1, it is contemplated that a dsRNA construct targeting other *Helicoverpa/Heliothis* species would control that respective insect, e.g. the *Helicoverpa* assulta PBAN/pyrokinin corresponding to GenBank accession number U96761/AY052417. Additionally it is contemplated that a single dsRNA construct would be effective in controlling a plurality of insect species.

EXAMPLE 1

Constructing dsRNA Construct for *Helicoverpa zea*

Cloning and Sequencing of Hez-PBAN/Pyrokinin Gene from *Helicoverpa zea*

A mRNA was isolated from the dissected brain-subesophageal ganglion (Br-SGs) of the adult moths (*Helicoverpa zea*) by Micro Fast mRNA purification kit (Invitrogen), and used to synthesize cDNA with the GeneRacer cDNA synthesis kit (Invitrogen). Cloning the full length Hez-PBAN cDNA was carried out using Generacer kit (Invitrogen) as described by the manufacturer. The primers, 5'-AAGATGTTCAATCAAACTCAGTTG-3' (SEQ. ID. NO. 12) and 5'-AAATTATGTTGATCGCGTTTTGTTTGT-3' (SEQ. ID. NO. 13) were designed from the sequence registered on the GenBank (Accession number: U08109). PCR was performed with the following temperature program: 33 cycles at 95° C. for 30 s, 52° C. for 30 s, and 72° C. for 1 min. The PCR product was gel purified and cloned using TOPO TA cloning kit (Invitrogen) and sequenced. The obtained full-length sequence information was aligned and sequences compared with our partial sequence using DNA analysis software.
Construction of Hez-PBAN/Pyrokinin dsRNA Construct and dsGFP Control
To construct Hez-PBAN dsRNA PCR primer set was designed 5'-T7-appended: 5'-TAATACGACTCAC-TATAGGG GTGTTTGCATTGTGTACCGC-3' (SEQ. ID. NO. 14), and 5'-TAATACGACTCACTATAGGGTATAG-GAAG GGGTTGATGGC-3' (SEQ. ID. NO. 15), to amplify 508-bp of Hez-PBAN DNA, which serves as the template for dsRNA synthesis using the MEGAscript RNA kit (Ambion). For a negative control, a green fluorescence protein (GFP) dsRNA was purchased from Ambion or was synthesized from a 546-bp GFP DNA template amplified by these primers 5'-TAATACGACTCACTATAGGGACGTAAA CGGCCACA AGTTC-3' (SEQ. ID. NO. 16) and 5'-TAATACGACTCACTATAGGGTGCTCAGGTAGTG-GTTGTCG-3' (SEQ. ID. NO. 17) using the same kit as above. The length of Hez-PBAN dsRNA (SEQ. ID. NO. 2 and SEQ. ID. NO. 3) was constructed from the full length of Hez-PBAN cDNA, 585-bp (SEQ. ID. NO. 1). Additionally a siRNA 25 base pair construct from Hez-PBAN dsRNA SEQ. ID. NO. 2 and SEQ. ID. NO. 3 to yield SEQ. ID. NO. 4 and SEQ. ID. NO. 5.

EXAMPLE 2

Oral Feeding Hez-PBAN dsRNA to Larval *Helicoverpa zea* Bioassay

The dsRNA constructs of SEQ. ID. NO. 2, SEQ. ID. NO. 3, SEQ. ID. NO. 4, and SEQ. ID. NO. 5 were mixed in an artificial diet for *Helicoverpa zea* as detailed at concentrations of 0.1 µg/g diet, 1.0 µg/g diet, and 10 µg/g diet. Control for dsRNA was compared against a dsGFP diet of 0.1 µg/g diet, 1.0 µg/g diet, and 10 µg/g diet. As detailed in FIG. 1, dsRNA constructs of SEQ. ID. NO. 2 and SEQ. ID. NO. 3 included in a *Helicoverpa zea* feed diet at the listed concentration exhibited greater mortality than a control diet. dsGFP diet of 0.1 µg/g diet and 1010 µg/g diet was not significantly different from the control *Helicoverpa zea* feed diet, however dsGFP at 1 μg/g diet was significantly greater than the control *Helicoverpa zea* feed diet.

As detailed in FIG. 2, the dsRNA constructs of SEQ. ID. NO. 4 and SEQ. ID. NO. 5 included in a *Helicoverpa zea* feed diet at the listed concentration. At feed concentrations of 1.0 μg/g diet and 10 μg/g diet, SEQ. ID. NO. 4 and SEQ. ID. NO. 5 showed statistical significance in larval mortality from a control diet. Similarly, a diet of SEQ. ID. NO. 2 and SEQ. ID. NO. 3 at a concentration of 0.10 μg/g diet also showed statistical significance in larval mortality from a control diet. At a feed diet of 0.10 μg/g SEQ. ID. NO. 4 and SEQ. ID. NO. 5 exhibited no statistical significance in larval mortality from a control diet.

EXAMPLE 3

Constructing dsRNA Construct for *Heliothis virescens*

Cloning and Sequencing of Hez-PBAN/Pyrokinin Gene from *Heliothis virescens*

Brain-subesophageal ganglia of 1 to 3-day old *H. virescens* female moths were dissected to isolate mRNA using MicroFast mRNA purification kits (Invitrogen). Isolated mRNA was used to amplify a full length (588-nucleotide) (SEQ. ID. NO. 6) of *H. virescens* PBAN cDNA with primer set 5'-ATGTTCTATCAAACACAGTTATT CGT-3' (SEQ. ID. NO. 18) and 5'-TTACGTTGATCGCGTTTTGTTTGTGC-3' (SEQ. ID. NO. 19) by one-step reverse transcription-polymerase chain reaction (RT-PCR) (Invitrogen kit) under one cycle at 50° C. for 30 min and 40 cycles of 95° C. for 20 s, 53° C. for 30 s, and 72° C. for 1 min. The PCR product was gel purified and used to amplify 476-nucleotide a DNA template of the PBAN dsRNA with primer set appended T7 promoter underlined 5'-<u>TAATACGACTCACTATAGGG</u>CCGTCTTTGCGACTACCAGT-3' (SEQ. ID. NO. 20) and 5'-<u>TAATACGACTCACTATAGGG</u>AAGTCGTGGGGAGAAGTTCA-3' (SEQ. ID. NO. 21) under 35 cycles of 95° C. for 30 s, 53° C. for 30 s, and 72° C. for 1 min. The PCR product was gel purified and cloned into pCR 2.1 TOPO vector (Invitrogen) and sequenced as SEQ. ID. NO. 7 and SEQ. ID. NO 8. The vector containing the DNA fragment was served for dsRNA synthesis using the MEGAscript RNA kit (Ambion).

EXAMPLE 4

Feeding Hev-PBAN dsRNA to Larval *Heliothis virescens* Bioassay

Figure 3:
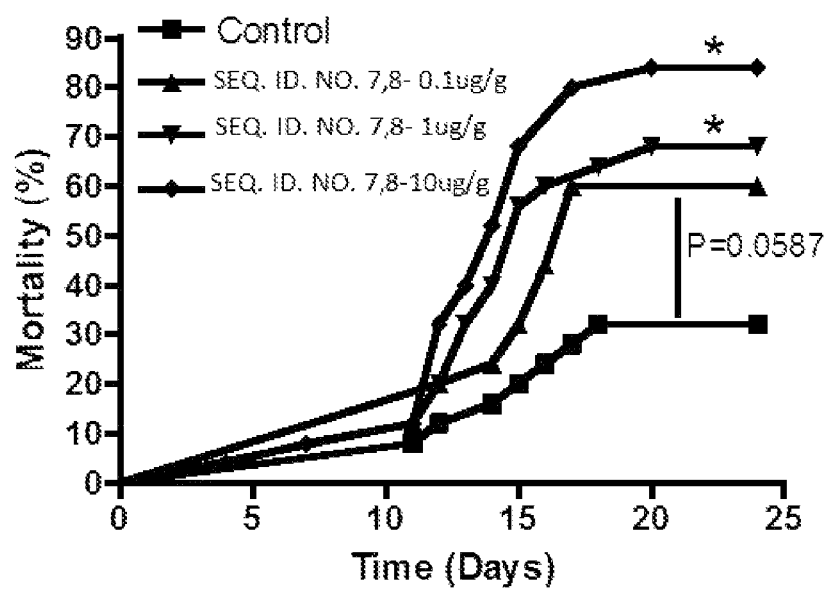
FIG. 3 is a graph depicting Heliothis virescens larval mortality from first instar to just prior to pupation fed dsRNA concentrations of 0.1 µg/1 g, 1 µg/1 g, or 10 µg/1 g of SEQ. ID. NO 7 and 8. The Heliothis virescens control was fed standard CEW diet (BioServe). Mortality curves were compared using the standard Kaplan-Meier Survival Analysis (GraphPad). Mortality for the SEQ. ID. NO 7 and 8 at 1 µg/1 g and control was significantly different: Logrank test: $\chi^2=4.853$, df=1, P=0.0276; therefore the SEQ. ID. NO 7 and 8 at 10 µg/1 g concentration was also significantly different from control. The SEQ. ID. NO 7 and 8 at 0.1 µg/1 g treatment was almost significantly different from control (Logrank test: $\chi^2=3.575$, df=1, P=0.0587).

The dsRNA constructs of SEQ. ID. NO. 7 and SEQ. ID. NO. 8 were mixed in an artificial diet for *Heliothis virescens* as detailed at concentrations of 0.1 μg/g diet, 1.0 μg/g diet, and 10 μg/g diet. Control for dsRNA was compared against a dsGFP diet of 0.1 μg/g diet, 1.0 μg/g diet, and 10 μg/g diet. As detailed in FIG. 3, dsRNA constructs of SEQ. ID. NO. 7 and SEQ. ID. NO. 8 at feed concentrations of 1.0 μg/g diet and 10 μg/g diet showed statistical significance in larval mortality from a control diet. A diet of SEQ. ID. NO. 7 and SEQ. ID. NO. 8 at a concentration of 0.10 μg/g diet was almost significantly different from control (Logrank test: $\chi^2$=3.575, df=1, P=0.0587). Control for dsRNA was compared against a dsGFP diet of 0.1 μg/g diet, 1.0 μg/g diet, and 10 μg/g diet and the three concentrations did not show a significantly difference from the standard control.

EXAMPLE 5

Constructing dsRNA Construct for *Helicoverpa armigera*

Cloning and Sequencing of HeA-PBAN/Pyrokinin Gene from *Helicoverpa armigera*

The *Helicoverpa armigera* PBAN gene sequence (AY043222, 639 bp) was obtained from Genbank (www.ncbi.nlm.nih.gov/). A synthetic gene was produced and cloned into a shuttle plasmid pCED51. Synthesis of 500 bp dsRNA was carried out using the Megascript RNAi kit (Ambion) following the manufacturer's protocol and using as a template a PCR product amplified from the plasmid pCED51. The forward primer used was PBAN_Ha_T7_F:

(SEQ. ID. NO. 22)
5' TAATACGACTCACTATAGGGTATTCACTACGAGCAGTGTT and the reverse primer was PBAN_Ha_T7_R: 5'

(SEQ. ID. NO. 23)
TAATACGACTCACTATAGGGTGGCATCATATCATAAGACAG.

dsRNA was then precipitated with 100% ethanol and sodium acetate 3M, pH5.2, washed 2 times with 70% ethanol and the pellets were resuspended in RNase free water. The PCR product was gel purified and cloned into pCR 2.1 TOPO vector (Invitrogen) and sequenced as SEQ. ID. NO. 10 and SEQ. ID. NO 11.

EXAMPLE 6

Feeding HeA-PBAN dsRNA to Larval *Helicoverpa armigera* Bioassay

Figure 4:
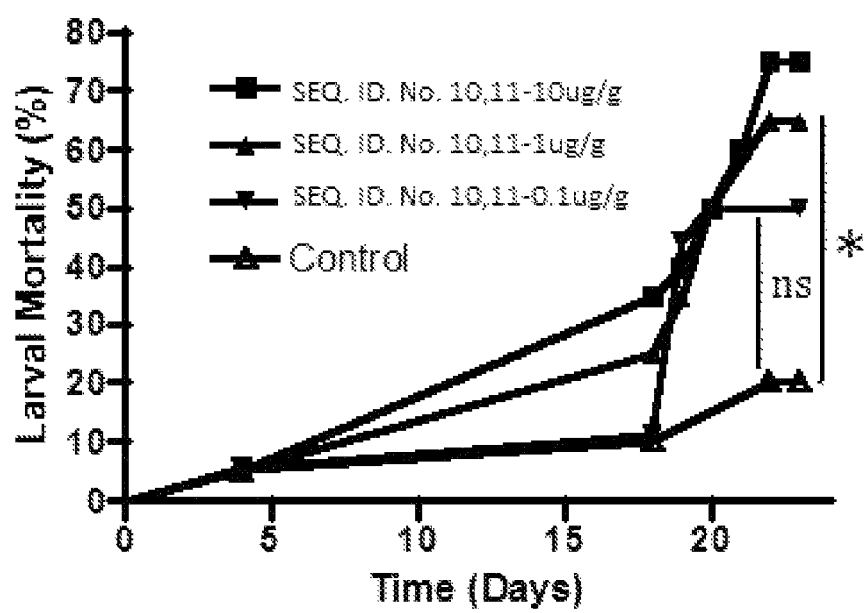
FIG. 4 is a graph depicting Heliothis armigera larval mortality from first instar to just prior to pupation fed dsRNA concentrations of 0.1 µg/1 g, 1 µg/1 g, or 10 µg/1 g of SEQ. ID. NO 10 and 11. Mortality curves were compared using the standard Kaplan-Meier Survival Analysis (GraphPad). The Treatments showed a positive concentration—activity relationship. However, the 0.1 µg/g concentration was not significantly different from the control: Logrank test: $\chi^2=0.1753$, df=1, P=0.6754. The 1.0 µg/g concentration was statistically different from control (Logrank test: $\chi^2=8.223$, df=1, P=0.0041) and by inference the 10.0 µg/g concentration is statistically different from control.
Figure 5:
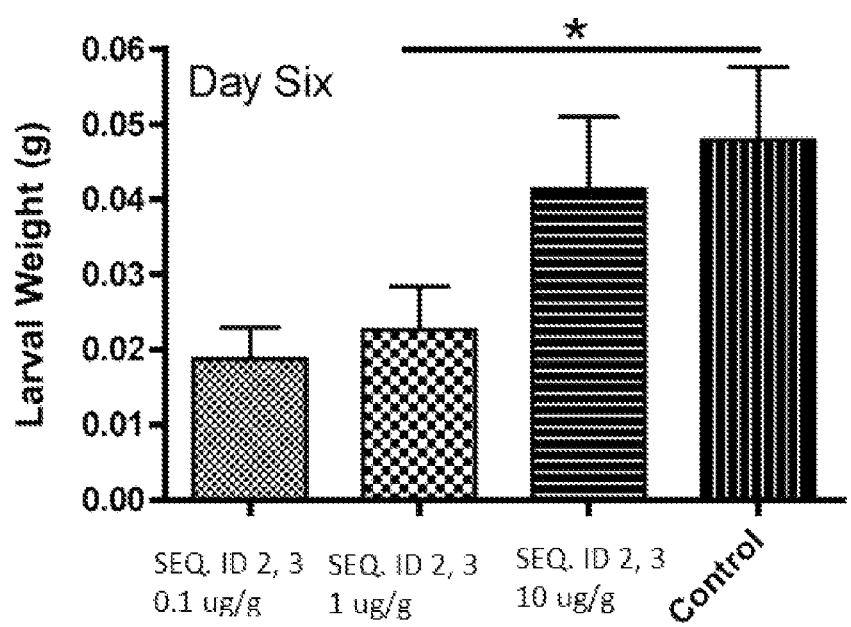
FIG. 5 is a graph depicting Helicoverpa zea larval weight differences between dsPBAN/pyrokinin treatments of dsRNA concentrations of 0.1 µg/1 g, 1 µg/1 g, or 10 µg/1 g of SEQ. ID. NO 2 and 3 and the standard control. The mean larval weight associated with the highest concentration of the PBAN treatment was not significantly different from the control (Two-tailed t-test: t=−0.4113, df=39, P=0.6330). However, the mean larval weight of the middle PBAN treatment concentration was significantly less than the control (Two-tailed t-test: t=2.107, df=36, P=0.0421) and by inspection and inference the lowest PBAN treatment concentration (0.1 ug/g) is also significantly less than the control.
Figure 6:
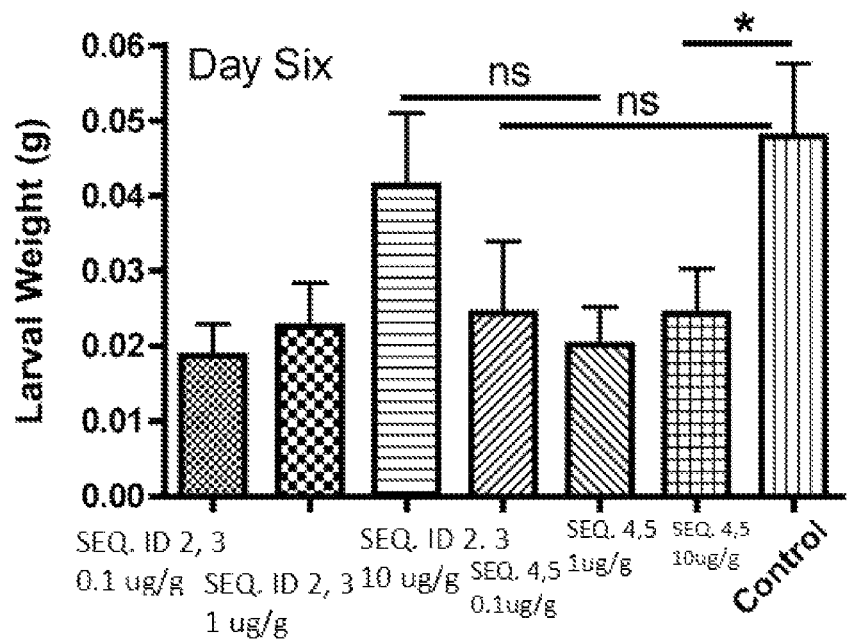
FIG. 6 is a graph depicting Helicoverpa zea larval weight differences the larval weight differences between PBAN treatments and a 25 bp siRNA (SEQ. ID. NO. 4 and 5) derived from the PBAN/pyrokinin RNAi. The 1.0 and 10 ug/g diet siRNA concentrations resulted in mean larval weights that were significantly different from the standard control (Control vs 507-10: Two-tailed t-test: t=2.072, df=40, P=0.0448). By inference the 1.0 ug concentration of SEQ. ID. NO. 4 and 5 is also significantly different from the control; however, the, 0.1 ug/g concentration was not significantly different from the control (Two-tailed t-test: t=1.727, df=38, P=0.0924).

The dsRNA constructs of SEQ. ID. NO. 10 and SEQ. ID. NO. 11 were mixed in an artificial diet for *Helicoverpa armigera* as detailed at concentrations of 0.1 μg/g diet, 1.0 μg/g diet, and 10 μg/g diet. Control for dsRNA was compared against a dsGFP diet of 0.1 μg/g diet, 1.0 μg/g diet, and 10 μg/g diet. As detailed in FIG. 4, dsRNA constructs of SEQ. ID. NO. 10 and SEQ. ID. NO. 11 included in a *Helicoverpa armigera* feed diet at 1.0 μg/g diet, and 10 μg/g diet exhibited greater mortality than a control diet. A diet of SEQ. ID. NO. 10 and SEQ. ID. NO. 11 at a concentration of 0.10 μg/g diet was not significantly different from the control diet. Control for dsRNA was compared against a dsGFP diet of 0.1 μg/g diet, 1.0 μg/g diet, and 10 μg/g diet and the three concentrations were not significantly different from the standard control.

While the invention has been described with reference to details of the illustrated embodiment, these details are not intended to limit the scope of the invention as defined in the appended claims. All cited references and published patent applications cited in this application are incorporated herein by reference. The embodiment of the invention in which exclusive property or privilege is claimed is defined as follows:

The invention claimed is:

1. A double-stranded ribonucleic acid (dsRNA) comprising a sense region comprising a sequence with at least 99% sequence identity to at least 21 consecutive nucleotides of SEQ ID NO: 7 or SEQ ID NO: 8, and an antisense region comprising a second sequence complementary to said sense region.

2. A DNA comprising a promoter functional in a host cell, and a DNA encoding a dsRNA comprising a first and a second region, wherein said first region comprises a sequence with at least 99% sequence identity to a portion of at least 21 consecutive nucleotides of SEQ ID NO: 7, or SEQ ID NO: 8, and wherein said second region is complementary to said first region.

3. The DNA of claim 2 wherein said host cell is a bacterial cell, a yeast cell, or a plant cell.

4. A host cell comprising the DNA of claim 2 or 3.

5. A chimeric gene comprising the following operably linked DNA:
   (a) a plant-expressible promoter;
   (b) a DNA region which when transcribed yields a double-stranded RNA molecule targeting a PBAN/pyokinin gene of a *Heliothis* insect, said RNA molecule comprising a first and second RNA region wherein:
      (i) said first RNA region comprises a nucleotide sequence of at least 99% sequence identity to at least 21 consecutive nucleotides of SEQ ID NO: 7 or SEQ ID NO: 8;
      (ii) said second RNA region comprises a nucleotide sequence complementary to said first RNA region; and
      (iii) said first and second RNA region are capable of base-pairing to form a double-stranded RNA molecule; and
   (c) optionally, a 3' end region comprising transcription termination and polyadenylation signals functioning in plant cells.

6. The chimeric gene of claim 5, wherein said first RNA region comprises at least 21 consecutive nucleotides of SEQ ID NO: 7.

7. The chimeric gene of claim 5, wherein between said first and second RNA region, a spacer region containing a plant intron is present.

8. The chimeric gene of claim 5, wherein said promoter is a constitutive promoter.

9. A plant cell, plant or seed comprising the chimeric gene of claim 5 or the double-stranded RNA molecule described in claim 5.

10. A method to control a *Heliothis*, comprising applying to or in a material on which such insect feeds, a dsRNA targeted to a PBAN/pyrokinin gene of said insect, wherein said dsRNA comprises the dsRNA of claim 1.

11. A method of controlling a *Heliothis* insect, comprising planting or growing plants expressing a dsRNA that targets a PBAN/pyrokinin gene of said insect, wherein said dsRNA comprises the dsRNA of claim 1.

12. A method for controlling a *Heliothis* species insect, the method comprising: applying a solution comprising copies of a double-stranded ribonucleic acid construct that targets a PBAN/Pyrokinin gene in said insect to plants or material on which said insect feeds, and wherein said dsRNA comprises the dsRNA of claim 1.

13. The method of claim 12, wherein said double-stranded ribonucleic acid targets the nucleotide sequence of SEQ ID NO: 7, or SEQ ID NO: 8.

* * * * *

SEQUENCE LISTING

```
<160> NUMBER OF SEQ ID NOS: 23

<210> SEQ ID NO 1
<211> LENGTH: 585
<212> TYPE: DNA
<213> ORGANISM: Helicoverpa zea

<400> SEQUENCE: 1
atgttcaatc aaactcagtt gtttgttttt ctcgctgtat tcactacgag cagtgtttta      60
gggaataaca atgatgttaa ggatggcgca gcgagtggag ctcacagcga ccgactaggt     120
ctttggttcg gtccccggct aggcaagcgc tcgctcagaa tatctaccga agataacaga     180
caagcattct tcaaattact cgaagccgcc gacgctttga aatactatta cgaccagcta     240
ccttatgaga tgcaagctga tgaacctgaa accagggtca ccaagaaggt gatcttcacc     300
```

```
cccaagttag gcagaagcct cgcatacgat gacaaaagct tgagaacgt ggagttcacg      360 cccagactcg gcaggagact gtccgatgat atgcctgcca cccccgctga ccaggaaatg    420
taccgccaag accctgaaca gattgacagc aggacaaagt acttctcccc aaggctcggc    480
agaaccatga acttctcacc acgactcggc agggaactgt cttatgatat gatgccaaat   540
aaaatcaggg tagtcaggag tacaaacaaa acgcgatcaa cataa                    585
```

<210> SEQ ID NO 2
<211> LENGTH: 508
<212> TYPE: RNA
<213> ORGANISM: Helicoverpa zea

<400> SEQUENCE: 2

```
caaugauguu aaggauggcg cagcgagugg agcucacagc gaccgacuag gucuuugguu    60 cggucccgg cuaggcaagc gcucgcucag auuaucuacc gaagauaaca gacaagcauu    120
cuucaaauua cucgaagccg ccgacgcuuu gaaauacuau uacgaccagc uaccuuauga   180
gaugcaagcu gaugaaccug aaaccagggu caccaagaag gugaucuuca cccccaaguu   240
aggcagaagc cucgcauacg augacaaaag cuugagaac guggaguuca cgcccagacu    300
cggcaggaga cuguccgaug auaugccugc cacccccgcu gaccaggaaa uguaccgcca    360
agacccugaa cagauugaca gcaggacaaa guacuucucc ccaaggcucg gcagaaccau   420
gaacuucuca ccacgacucg gcagggaacu gucuuaugau augaugccaa auaaaaucag   480
gguagucagg aguacaaaca aaacgcga                                       508
```

<210> SEQ ID NO 3
<211> LENGTH: 508
<212> TYPE: RNA
<213> ORGANISM: Helicoverpa zea

<400> SEQUENCE: 3

```
guuacuacaa uuccuaccgc gucgcucacc ucgaguguc cuggcugauc cagaaaccaa     60 gccagggcc gauccguucg cgagcgaguc uuauagaugg cuucuauugu cuguucguaa    120
gaaguuuaau gagcuucggc ggcugcgaaa cuuuaugaua augcuggucg auggaauacu   180
cuacguucga cuacuuggac uuuggucca guggucuuc cacuagaagu ggggguucaa    240
uccgucuucg gagcguaugc uacuguuuuc gaaacucuug caccucaagu gcgggucuga   300
gccguccucu gacaggcuac uauacggacg gugggggcga cugguccuuu acauggcggu   360
ucugggacuu gucuaacugu cguccuguuu caugaagagg gguuccgagc cgucuuggua   420
cuugaagagu ggugcugagc cgucccuuga cagaauacua uacuacgguu uauuuaguc   480 ccaucaguccu ucauguuugu uuugcgcu                                      508
```

<210> SEQ ID NO 4
<211> LENGTH: 25
<212> TYPE: RNA
<213> ORGANISM: Helicoverpa zea

<400> SEQUENCE: 4

```
cggcagggaa cugucuuaug auaug                                          25
```

<210> SEQ ID NO 5
<211> LENGTH: 25
<212> TYPE: RNA
<213> ORGANISM: Helicoverpa zea

<400> SEQUENCE: 5
gccgucccuu gacagaauac uauac 25

<210> SEQ ID NO 6
<211> LENGTH: 588
<212> TYPE: RNA
<213> ORGANISM: Heliothis virescens

<400> SEQUENCE: 6
auguucuauc aaacacaguu auucguuuuc cucgccgucu uugcgacuac caguguuuua 60
ggaaauaaua augaugauaa ggauggcgcc gccagcgggg cgcacaguga ucgauuaggc 120
cuuugguucg gucccagguu aggcaaacga ucucucagga uaucuacggg agacaacagg 180
caagcauucu ucaaacuacu ggaagcagcc gacgcuuuga aauacuacua cgaccagcug 240
ccuuaugaga ugcaagcuga ugaccccgaa accaggguga ccaagaaggu caucuucacc 300
cccaaguuag gcagaagccu uucauaugac gacaagagcu uugaaaaugu ggaauucacg 360
cccaggcucg gaagaagauu agcugaugau augcccgcca cuccugcaga ccaggaaaug 420
uaccgccaag acccugaaca gaucgacagc aggaggacaa aguacuucuc cccaagacuu 480
ggcaggacua ugaacuucuc cccacgacuu ggcagggaac ugacuuauga uaugcugcca 540
aacaaaauua gggucguaag gagcacaaac aaaacgcgau caacguaa 588

<210> SEQ ID NO 7
<211> LENGTH: 476
<212> TYPE: RNA
<213> ORGANISM: Heliothis virescens

<400> SEQUENCE: 7
ccgucuuugc gacuaccagu guuuuaggaa auaauaauga ugauaaggau ggcgccgcca 60
gcggggcgca cagugaucga uuaggccuuu gguucggucc cagguuaggc aaacgaucuc 120
ucaggauauc uacgggagac aacaggcaag cauucuucaa acuacuggaa gcagccgacg 180
cuuugaaaua cuacuacgac cagcugccuu augagaugca agcugaugac cccgaaacca 240
gggugaccaa gaaggucauc uucacccccca aguuaggcag aagccuuuca uaugacgaca 300
agagcuuuga aaauguggaa uucacgccca ggcucggaag aagauuagcu gaugauaugc 360
ccgccacucc ugcagaccag gaaauguacc gccaagaccc ugaacagauc gacagcagga 420
ggacaaagua cuucucccca agacuuggca ggacuaugaa cuucucccca cgacuu 476

<210> SEQ ID NO 8
<211> LENGTH: 476
<212> TYPE: RNA
<213> ORGANISM: Heliothis virescens

<400> SEQUENCE: 8
ggcagaaacg cugaugguca caaaauccuu uauuauuacu acuauuccua ccgcggcggu 60
cgccccgcgu gucacuagcu aauccggaaa ccaagccagg guccaauccg uuugcuagag 120
aguccuauag augcccucug uuguccguuc guaagaaguu ugaugaccuu cgucggcugc 180
gaaacuuuau gaugaugcug gucgacggaa uacucuacgu ucgacuacug gggcuuuggu 240
cccacugguu cuuccaguag aaguggggu ucaauccguc uucggaaagu auacugcugu 300
ucucgaaacu uuuacaccuu aagugcgggu ccgagccuuc uucuaaucga cuacuauacg 360
ggcggugagg acgucugguc cuuuacaugg cgguucuggg acuugucuag cugucguccu 420
ccuguuucau gaagaggggu ucugaaccgu ccugauacuu gaagaggggu gcugaa 476

```
<210> SEQ ID NO 9
<211> LENGTH: 639
<212> TYPE: DNA
<213> ORGANISM: Heliothis armigera

<400> SEQUENCE: 9
atcgttcatt ccatgatgtt caatcaaact cagttgtttg tttttctcgc tgtattcact      60
acgagcagtg ttttagggaa taacaatgat gttaaggatg gcgcagcgag cggggcgcac     120
agcgaccgac taggcctttg gttcggtccc agactaggca agcgctctct caggatatct     180
accgaagata acagacaagc attcttcaaa ttactggaag ctgccgacgc tttgaaatac     240
tattacgacc agctacctta tgaaatgcaa gctgatgaac ctgaaaccag ggtgaccaag     300
aaggtgatct tcaccccgaa gttaggcaga agcctcgcat acgatgacaa gagctttgaa     360
aacgtggagt ttactcctag actcggcagg agactgtctg atgatatgcc tgccactccc     420
gctgaccagg aaatgtaccg ccaagaccct gaacaaattg acagcaggac gaaatacttc     480
tccccaaggc taggcagaac catgaacttc tcaccacgac tcggcaggga actgtcttat     540
gatatgatgc caaacaaaat cagggtagta aggagtgcaa acaaaacgcg atcaacataa     600
tttggagcaa aacaagacg caaagctagt ctaacctca                             639

<210> SEQ ID NO 10
<211> LENGTH: 500
<212> TYPE: RNA
<213> ORGANISM: Heliothis armigera

<400> SEQUENCE: 10
uggcaucaua ucauaagaca guucccugcc gagucguggu gagaaguuca gguucugcc       60
uagccuuggg gagaaguauu ucguccugcu gucaauuugu cagggucuu ggcgguacau      120
uuccuggucu acgggagugg caggcauauc aucagacagu cuccugccga gucuaggagu     180
aaacuccacg uuuucaaagc ucuugucauc guaugcgagg cuucugccua acuucggggu     240
gaagaucacc uucuuggucu cccugguuuc agguucauca gcuugcauuu cauaagguag     300
cuggucguaa uaguauuuca aagcgucggc agcuuccagu aauuugaaga augcuugucu     360
guuaucuucg guagauaucc ugagagagcg cuugccuagu cugggaccga accaaaggcc     420
uagucggucg cugugcgccc cgcucgcugc gccauccuua acaucauugu uauucccuaa     480
aacacugcuc guagugaaua                                                 500

<210> SEQ ID NO 11
<211> LENGTH: 500
<212> TYPE: RNA
<213> ORGANISM: Heliothis armigera

<400> SEQUENCE: 11
accguaguau aguauucugu caagggacgg cucagcacca cucuucaagu accaagacgg      60
aucggaaccc cucuucauaa agcaggacga caguuaaaca aguccccagaa ccgccaugua    120
aaggaccagu cgcccucacc guccguauag uagucugucu gaggacgcu cagauccuca     180
uuugagggugc aaaaguuucg agaacaguag cauacgcucc gaagacggau ugaagcccca    240
cuucuagugg aagaaccagu gggaccaaag uccaaguagu cgaacguaaa guauuccauc     300
gaccagcauu aucauaaagu uucgcagccg ucgaagguca uuaaacuucu uacgaacaga    360
caauagaagc caucuauagg acucucucgc gaacggauca gacccuggcu ugguuuccgg     420
```

```
aucagccagc gacacgcggg gcgagcgacg cgguaggaau uguaguaaca auaagggauu    480
uugugacgag caucacuuau                                                500
```

<210> SEQ ID NO 12
<211> LENGTH: 24
<212> TYPE: DNA
<213> ORGANISM: Helicoverpa zea

<400> SEQUENCE: 12

```
aagatgttca atcaaactca gttg                                           24
```

<210> SEQ ID NO 13
<211> LENGTH: 27
<212> TYPE: DNA
<213> ORGANISM: Helicoverpa zea

<400> SEQUENCE: 13

```
aaattatgtt gatcgcgttt tgtttgt                                        27
```

<210> SEQ ID NO 14
<211> LENGTH: 40
<212> TYPE: DNA
<213> ORGANISM: Helicoverpa zea

<400> SEQUENCE: 14

```
taatacgact cactataggg gtgtttgcat tgtgtaccgc                           40
```

<210> SEQ ID NO 15
<211> LENGTH: 40
<212> TYPE: DNA
<213> ORGANISM: Helicoverpa zea

<400> SEQUENCE: 15

```
taatacgact cactataggg tataggaagg ggttgatggc                           40
```

<210> SEQ ID NO 16
<211> LENGTH: 40
<212> TYPE: DNA
<213> ORGANISM: Helicoverpa zea

<400> SEQUENCE: 16

```
taatacgact cactataggg acgtaaacgg ccacaagttc                           40
```

<210> SEQ ID NO 17
<211> LENGTH: 40
<212> TYPE: DNA
<213> ORGANISM: Helicoverpa zea

<400> SEQUENCE: 17

```
taatacgact cactataggg tgctcaggta gtggttgtcg                           40
```

<210> SEQ ID NO 18
<211> LENGTH: 26
<212> TYPE: DNA
<213> ORGANISM: Heliothis virescens

<400> SEQUENCE: 18

```
atgttctatc aaacacagtt attcgt                                         26
```

<210> SEQ ID NO 19
<211> LENGTH: 26
<212> TYPE: DNA
<213> ORGANISM: Heliothis virescens

```
-continued

<400> SEQUENCE: 19
ttacgttgat cgcgttttgt ttgtgc                                          26

<210> SEQ ID NO 20
<211> LENGTH: 40
<212> TYPE: DNA
<213> ORGANISM: Heliothis virescens

<400> SEQUENCE: 20
taatacgact cactataggg ccgtctttgc gactaccagt                           40

<210> SEQ ID NO 21
<211> LENGTH: 40
<212> TYPE: DNA
<213> ORGANISM: Heliothis virescens

<400> SEQUENCE: 21
taatacgact cactataggg aagtcgtggg gagaagttca                           40

<210> SEQ ID NO 22
<211> LENGTH: 40
<212> TYPE: DNA
<213> ORGANISM: Heliothis armigera

<400> SEQUENCE: 22
taatacgact cactataggg tattcactac gagcagtgtt                           40

<210> SEQ ID NO 23
<211> LENGTH: 41
<212> TYPE: DNA
<213> ORGANISM: Heliothis armigera

<400> SEQUENCE: 23
taatacgact cactataggg tggcatcata tcataagaca g                         41
```